(12) United States Patent
Bleda et al.

(10) Patent No.: US 7,772,396 B2
(45) Date of Patent: Aug. 10, 2010

(54) PROCESS FOR THE RESOLUTION OF ZOPICLONE AND INTERMEDIATE COMPOUNDS

(75) Inventors: David Fernández Bleda, Sant Pere de Ribes (ES); Jordi Lluis Tous, Tarragona (ES)

(73) Assignee: Esteve Quimica, S.A. Avda. Mare de deu de Monsterrat, Barcelona (ES)

( * ) Notice: Subject to any disclaimer, the term of this patent is extended or adjusted under 35 U.S.C. 154(b) by 87 days.

(21) Appl. No.: 11/866,584

(22) Filed: Oct. 3, 2007

(65) Prior Publication Data

US 2009/0036681 A1    Feb. 5, 2009

(30) Foreign Application Priority Data

Aug. 2, 2007    (EP)    .................... 07380226

(51) Int. Cl.
    *C07D 471/00*    (2006.01)
(52) U.S. Cl. ............ 544/350; 544/360; 546/268.1
(58) Field of Classification Search ............ 544/350, 544/360; 546/268.1
    See application file for complete search history.

(56) References Cited

U.S. PATENT DOCUMENTS

| 3,862,149 A | 1/1975 | Cotrel et al. |
| 6,444,673 B1 | 9/2002 | Cotrel et al. |
| 6,969,767 B1 | 11/2005 | Jasanada et al. |
| 2007/0054914 A1 | 3/2007 | Mandava et al. |

FOREIGN PATENT DOCUMENTS

| WO | WO9212980 A1 | 8/1992 |
| WO | WO2005060968 A1 | 7/2005 |
| WO | WO2005079851 A2 | 9/2005 |
| WO | WO2005097132 A2 | 10/2005 |
| WO | WO2006136866 A1 | 12/2006 |
| WO | WO2007083188 A2 | 7/2007 |
| WO | WO2007088073 A1 | 8/2007 |
| WO | WO2007109799 A2 | 9/2007 |
| WO | WO2007124025 A2 | 11/2007 |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*
Gottfried Blaschke, Georg Hempel, and Walter E. Muller, Preparative and Analytical Separation of the Zopiclone Enantiomers and Determination of Their Affinity to the Benzodiazepine Receptor Binding Site, Chirality, 1993, pp. 419-421, vol. 5.
(+)-6-(5-chloro-2-pyridinyl)-7(S)-(4-methylpiperazin-1-yl-carbonyloxy)-6,7-dihydro-5H-pyrrolo-[3,4-b]pyrazine-5-one maleate salt Crystalline Form I and IV, published in English on Mar. 21, 2006 at IP.COM.

* cited by examiner

*Primary Examiner*—James O Wilson
*Assistant Examiner*—Douglas M Willis
(74) *Attorney, Agent, or Firm*—McNeely & Hare LLP; William D. Hare

(57) ABSTRACT

The present invention refers to a process for the resolution into one of its enantiomers of the racemate of compound of formula (I):

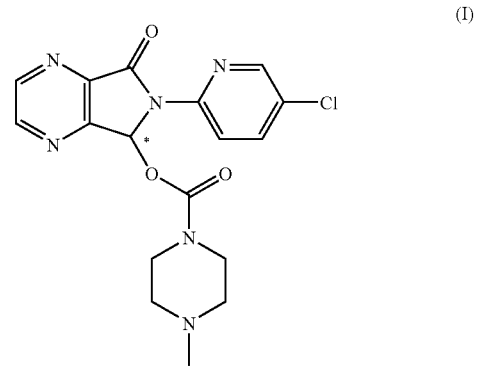

(I)

which comprises separating said one of its enantiomers from a diastereoisomeric salt of formula (II), which is formed by reaction of the racemic mixture with an optically active acetylated amino acid of formula (III). The invention also refers to new intermediates which are useful to carry out the process of the invention.

5 Claims, No Drawings

PROCESS FOR THE RESOLUTION OF ZOPICLONE AND INTERMEDIATE COMPOUNDS

CROSS-REFERENCE TO RELATED APPLICATIONS

This application claims priority from EP07380226.6, filed on Aug. 2, 2007.

FIELD OF THE INVENTION

The present invention refers to a new process for the resolution into one of its enantiomers of the racemic mixture of the compound zopiclone, 6-(5-chloro-2-pyridyl)-5-[(4-methyl-1-piperazinyl)carbonyloxy]-7-oxo-6,7-dihydro-5H-pyrrolo[3,4-b]pyrazine, and to intermediate compounds useful for carrying out said process.

BACKGROUND OF THE INVENTION

The compound 6-(5-chloro-2-pyridyl)-5-[(4-methyl-1-piperazinyl)carbonyloxy]-7-oxo-6,7-dihydro-5H-pyrrolo[3,4-b]pyrazine of general formula (I):

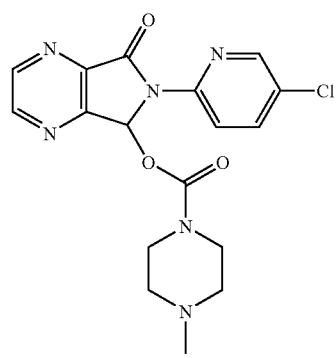

also known by the name zopiclone, is a commercial product characterized for its hypnotic, sedative, tranquilizing, anxiolytic, muscle-relaxant and anticonvulsant properties. This compound was described for the first time in French patent document FR2166314, which also describes a process for obtaining it as well as pharmaceutical compositions comprising said active ingredient.

The compound of formula (I) has an asymmetric carbon atom at the 5-position of the 5H-pyrrolo[3,4-b]pyrazine ring-system and, as a result, it must be considered, in racemic form, to consist of an equimolecular mixture of the laevorotatory and dextrorotatory forms. In a racemic product, it is widely known that, often, one of the two enantiomers is active and that an enhancement of the toxicity may be linked to this activity, the other enantiomer being both markedly less active or inactive and less toxic.

In the case of zopiclone, it was found that the dextrorotatory enantiomer (S-enantiomer) is approximately twice active as the racemate, while having a lower toxicity than that of the racemate, but that the laevorotatory isomer is both almost inactive and more toxic than the racemate.

The dextrorotatory isomer of zopiclone, also known as eszopiclone, may be prepared from the corresponding racemate according to usual methods, such as chiral-phase chromatography, resolution of an optically active salt, stereoselective enzymatic catalysis by means of an appropriate microorganism, or asymmetric synthesis.

The first reference describing a process for obtaining the different enantiomers of zopiclone is EP0609210. More specifically, this document refers to a process for obtaining the dextrorotatory isomer of zopiclone by resolution of racemic zopiclone by using an optically active acid, namely D-(+)-O,O'-dibenzoyl-tartaric acid, working in the presence of an appropriate organic solvent, isolating the salt of the dextrorotatory isomer, displacing this isomer from its salt and optionally, the conversion of said isomer into a pharmaceutically acceptable salt.

The scientific publication Chirality, 5, 419 (1993) and international applications WO2005/079851, WO2005/060968 and WO2005/097132 describe the resolution of the racemic mixture of zopiclone to afford eszopiclone by using malic acid as optically active acid in the presence of a mixture of acetone and methanol as organic solvents. The resulting (S)-zopiclone D-malate salt is converted to optically pure eszopiclone by treatment with aqueous potassium carbonate and ethyl acetate, followed by separation, crystallization and milling to the desired size.

The American patent application US2007/054914 refers to a method for the resolution of the racemic mixture of zopiclone by using di-p-toluoyl tartaric acid as optically active acid.

However, in spite of the existence of processes allowing the resolution of racemic zopiclone by fractionated crystallization using classic resolving agents, more specifically chiral acids, such as malic, dibenzoyltartaric and di-p-toluoyl tartaric acids, in organic solvents, these lead to compounds with low optical purity in a single crystallization and little reproducibility, what it makes necessary further crystallization processes to obtain high optical purities. Consequently, there is a serious need to develop improved processes which allows obtaining enantiomers of a higher optical purity.

BRIEF DESCRIPTION OF THE INVENTION

The authors of the present invention have surprisingly found that the resolution of the racemic mixture of the compound zopiclone can be achieved enantioselectively by reacting it with an optically acetylated amino acid. This process provides excellent diastereoisomeric excess and yields even in the first crystallization. Another advantage derived from using said acetylated amino acid, is that the eszopiclone salts obtained in the process of the invention are water soluble, which makes easier the work-up when isolating the desired enantiomer.

Therefore, an object of the present invention refers to a process (hereinafter referred as to the process of the invention) for the resolution into one of its enantiomers of the racemate of compound of formula (I):

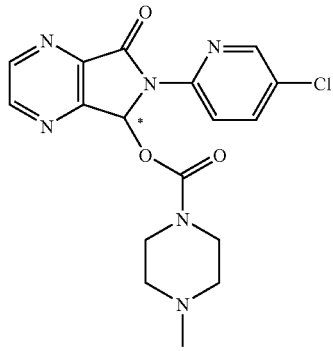

(I)

which comprises separating said one of its enantiomers from a diastereoisomeric salt of formula (II):

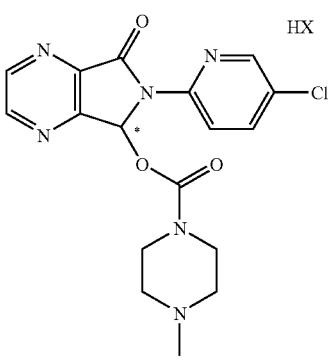

(II)

wherein HX is an optically active acetylated amino acid of formula (III):

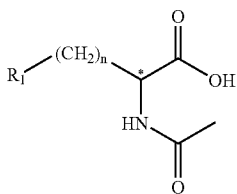

(III)

wherein:
n is 0, 1, 2 or 3,
$R^1$ is H, an alkyl group, an aryl group, a heteroaryl group, $CONH_2$, COOH, $SR^2$ or $OR^2$, wherein $R^2$ is a $C_1$-$C_6$ alkyl.

Another object of the invention refers to a process for the resolution into one of the enantiomers of the racemate of the compound of formula (I):

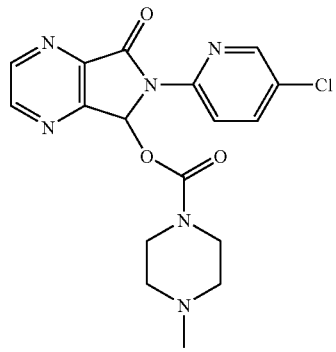

(I)

comprising the following steps:

a) reacting said racemate with any of the enantiomers of an optically active acetylated amino acid of formula (III):

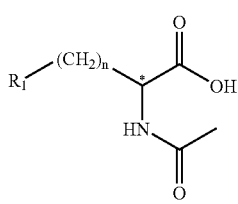

(III)

wherein n and $R^1$ are as defined above;

b) isolating an optically pure diastereoisomeric salt of formula (II):

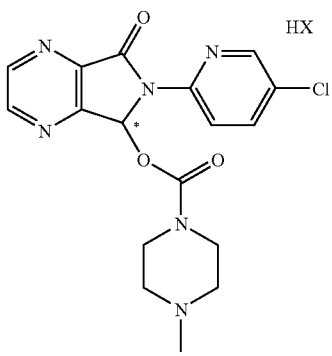

(II)

wherein HX is the optically active acetylated amino acid of formula (III); and c) separating an enantiomer of formula (I) from its diastereoisomeric salt of formula (II).

Finally, another object of the present invention relates to the diastereoisomeric salts of formula (II) constituting the intermediate compounds useful for carrying out the process described in the present invention. In a preferred aspect, said salts are (S)-zopiclone N-acetyl-D-glutamate, (S)-zopiclone N-acetyl-D-aspartate, (S)-zopiclone N-acetyl-D-methionate, (S)-zopiclone N-acetyl-L-glutamate, (S)-zopiclone N-acetyl-L-aspartate or (S)-zopiclone N-acetyl-L-methionate.

DETAILED DESCRIPTION OF THE INVENTION

In the above definition of compounds of formula (I) used in the present invention, the following terms have the meaning indicated:

"Alkyl" refers to a straight or branched hydrocarbon chain radical consisting of carbon and hydrogen atoms, containing no unsaturation, having one to eight carbon atoms, and which is attached to the rest of the molecule by a single bond, e. g., methyl, ethyl, n-propyl, i-propyl, n-butyl, t-butyl, n-pentyl, etc. The term "$C_1$-$C_6$ alkyl" is as defined for alkyl but having one to six carbon atoms.

"Aryl" refers to a phenyl, naphthyl, indenyl, fenanthryl or anthracyl radical, preferably phenyl or naphthyl radical.

"Heteroaryl" refers to an aromatic heterocyclic radical. The heterocycle refers to a stable 3- to 15-membered ring which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. Examples of such heterocycles include, but are not limited to, azepines, benzimidazole, benzothiazole, furan, isothiazole, imidazole, indole, piperidine, piperazine, purine, quinoline, thiadiazole, tetrahydrofuran.

The present invention describes a new, effective and simple process for the resolution into one of the enantiomers of the racemate of the compound 6-(5-chloro-2-pyridyl)-5-[(4-methyl-1-piperazinyl)carbonyloxy]-7-oxo-6,7-dihydro-5H-pyrrolo[3,4-b]pyrazine by means of fractionated crystallization of new intermediates corresponding to pure diastereoisomeric salts.

In a preferred embodiment of the invention, the optically active acetylated amino acid of formula (III), also defined as HX, is selected from N-acetyl-D-glutamic acid, N-acetyl-L-glutamic acid, N-acetyl-D-aspartic acid, N-acetyl-L-aspartic acid, N-acetyl-D-methionine and N-acetyl-L-methionine.

In a particular embodiment of the invention, the enantiomer obtained according to the process of the invention is the (S)-enantiomer. In this case, the diastereoisomeric salt of formula (II) is selected from (S)-zopiclone N-acetyl-D-glutamate, (S)-zopiclone N-acetyl-D-aspartate, (S)-zopiclone N-acetyl-D-methionate, (S)-zopiclone N-acetyl-L-glutamate, (S)-zopiclone N-acetyl-L-aspartate and (S)-zopiclone N-acetyl-L-methionate.

In another particular embodiment of the invention, the enantiomer obtained according to the process of the invention is the (R)-enantiomer. In this case, the diastereoisomeric salt of formula (II) is selected from (R)-zopiclone N-acetyl-L-glutamate, (R)-zopiclone N-acetyl-L-aspartate, (R)-zopiclone N-acetyl-L-methionate, (R)-zopiclone N-acetyl-D-glutamate, (R)-zopiclone N-acetyl-D-aspartate and (R)-zopiclone N-acetyl-D-methionate.

The racemic compound base used as the starting material for the resolution proposed in this document can be obtained by any process known in the state of the art. For example, said racemate can be obtained by a process such as described in French patent application FR2166314.

The resolution of the compound of formula (I):

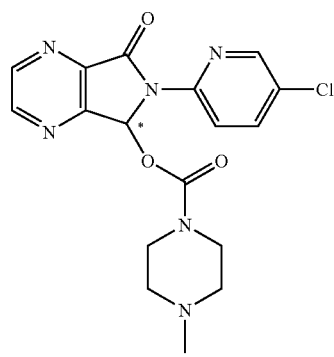

(I)

is carried out by means of reacting the racemate or any mixture of enantiomers of compound (I) with an optically pure acetylated amino acid of general formula (III):

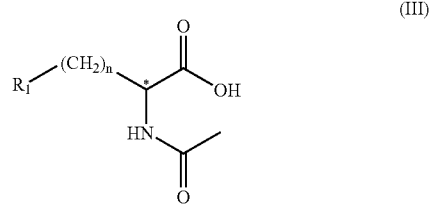

(III)

wherein n is 0, 1, 2 or 3, and $R^1$ is H, an alkyl group, an aryl group, a heteroaryl group, $CONH_2$, COOH, $SR^2$ or $OR^2$, wherein R is a $C_1$-$C_6$ alkyl, in an organic solvent or in a mixture of said organic solvents. Thus obtained are salts of formula (II):

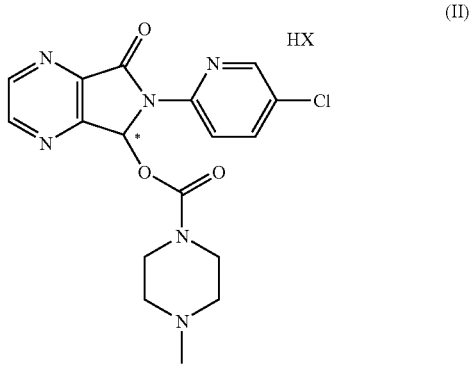

(II)

wherein HX is the acetylated amino acid of formula (III) which, by means of fractionated crystallization, is split into its pure diastereoisomeric salts.

The formation of the diastereoisomeric salts from racemic mixtures of the compound of formula (I) with any of the enantiomers of acetylated amino acids of formula (III) is carried out in the presence of an organic solvent or in a mixture of organic solvents. In a preferred embodiment of the invention, the organic solvent is selected from alcohols, ethers, esters, ketones, nitriles, halogenated solvents, aromatic solvents and mixtures thereof. Even in a more preferred embodiment, the organic solvent is selected form methanol, toluene, xylene, acetone, ethyl acetate, acetonitrile, tetrahydrofuran, isopropyl acetate, ethyl formiate, methyl tertbutyl ether, diethylcarbonate, chlorobenzene, dichloromethane and mixtures thereof.

In a variant of the process, if the dextrorotatory enantiomer of the acetylated amino acid is used, then the (S)-zopiclone N-acetyl-D-amino acid diastereoisomeric salt is firstly obtained. On the contrary, when the laevorotatory enantiomer of the acetylated amino acid is used, then the (R)-zopiclone N-acetyl-L-amino acid diastereoisomeric salt is firstly obtained.

Thus, in a particular embodiment of the invention, when N-acetyl-D-glutamic acid is used as optically active amino acid of formula (III), then (S)-zopiclone N-acetyl-D-glutamate is isolated in the step b) of the process. In another particular embodiment, when N-acetyl-L-glutamic acid is used as optically active amino acid of formula (III), then (R)-zopiclone N-acetyl-L-glutamate is isolated in step b). In another particular embodiment, when N-acetyl-D-aspartic acid is used as optically active amino acid of formula (III), then (S)-zopiclone N-acetyl-D-aspartate is isolated in step b). In another particular embodiment, when N-acetyl-L-aspartic acid is used as optically active amino acid of formula (III), then (R)-zopiclone N-acetyl-L-aspartate is isolated in step b). In another particular embodiment, when N-acetyl-D-methionine is used as optically active amino acid of formula (III), then (S)-zopiclone N-acetyl-D-methionate is isolated in step b). In another particular embodiment, when N-acetyl-L-methionine is used as optically active amino acid of formula (III), then (R)-zopiclone N-acetyl-L-methionate is isolated in step b).

Therefore, depending on the choice of the acetylated amino acid enantiomer of formula (III), one of the two possible diastereoisomeric salts is split in a first crystallization, the other diastereoisomeric salt remaining dissolved in the mother liquor, which could be also isolated. Therefore, another aspect of the invention refers to an additional isolation step of the other optically pure diastereoisomeric salt of formula (II). This additional isolation step of the other diastereoisomeric salt comprises the concentration of the mother liquor generated upon isolating the first diastereoisomeric salt and the subsequent crystallization so as to cause precipitation of the said other diastereoisomeric salt.

The salts obtained in any of the cases described above can be purified for the purpose of increasing their optical purity by simple resuspension or recrystallization in a suitable solvent.

In a particular embodiment of the invention, the (R)-enantiomer obtained from the process of the invention may be recycled in order to prepare the (S)-enantiomer. Thus, the process of the invention may further comprise an additional step of racemisation of the (R)-enantiomer to prepare the racemate of compound of formula (I). This step can be carried out by deprotonation of the chiral carbon of the (R)-enantiomer, thus obtaining a planar molecule which is susceptible to be converted again in a racemic compound. Once the racemate of formula (I) is obtained, then this compound is subjected to the steps a) to c) described above in order to isolate the (S)-enantiomer.

Another aspect of the present invention refers to an optically pure diastereoisomeric salt of formula (II):

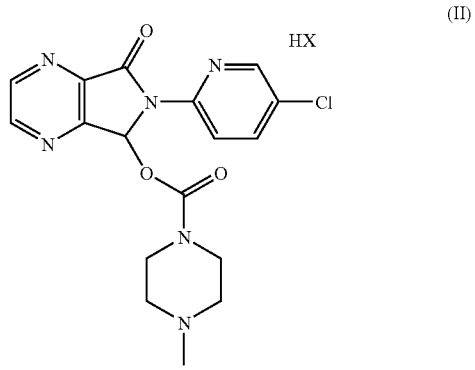

(II)

wherein HX is as defined above.

In a preferred embodiment, said salt of formula (II) is (S)-zopiclone N-acetyl-D-glutamate, (S)-zopiclone N-acetyl-D-aspartate, (S)-zopiclone N-acetyl-D-methionate, (S)-zopiclone N-acetyl-L-glutamate, (S)-zopiclone N-acetyl-L-aspartate or (S)-zopiclone N-acetyl-L-methionate.

The previously described process allows resolving the racemic mixture of the compound of formula (I) by obtaining any of the two enantiomers. The yields and optical purity of the obtained products, the simplicity of the operations and the reproducibility of the process make it applicable from the industrial point of view.

The following examples are provided only as an additional illustration of the invention and must not be taken as a definition of the limits thereof.

EXAMPLES

Example 1

Preparation of (S)-zopiclone N-acetyl-D-aspartate

A three-neck 500 ml flask was charged with 25 g of (±)-zopiclone (1 eq) and 11.3 g of N-acetyl-D-aspartic acid (1 eq). 363 ml of a mixture of methanol/toluene (1/1) were added. The reaction mixture was stirred for 10 minutes at room temperature, then heated and maintained for 30 minutes at reflux. The dispersion was slowly cooled and maintained for over 30 minutes at room temperature. The solid product was isolated by filtration and washed with 10 ml of methanol and 10 ml of toluene. The solid was dried under vacuum to obtain 15.6 g of (S)-zopiclone N-acetyl-D-aspartate (43%) as a white product.

Diastereoisomeric excess (d.e.): 99.5% by chiral HPLC. Water content: 0.6% w/w. Melting point: 186-189° C. $[\alpha]_D^{20}$: +55° (c 1% w/w water). IR (KBr, cm$^{-1}$): 3433, 1741, 1731, 1720, 1675, 1575, 1460, 1373, 1279, 1255, 1031. $^1$H-NMR (DMSO-d$_6$, 400 MHz) δ (ppm): 8.96 (1H, d, 2.4 Hz), 8.93 (1H, d, 2.4 Hz), 8.53 (1H, d, 2.4 Hz), 8.36 (1H, d, 9.2 Hz), 8.14 (1H, wide signal), 8.09 (1H, dd, 9.2 Hz, 2.4 Hz), 7.78 (1H, s), 4.47-4.41 (1H, m), 3.47 (1H, wide signal), 3.31 (1H, wide signal), 3.14 (2H, wide signal), 2.62 (1H, dd, 16.4 Hz, 6.4 Hz), 2.50 (1H, dd, 16.4 Hz, 6.4 Hz), 2.35 (1H, wide signal), 2.32 (1H, wide signal), 2.19 (1H, wide signal), 2.18 (3H, s), 1.89 (1H, wide signal), 1.81 (3H, s). $^{13}$C-NMR (DMSO-d$_6$, 100 MHz) δ (ppm): 172.7, 171.8, 169.0, 163.1, 155.4, 152.8, 148.6, 148.0, 147.8, 146.6, 143.4, 138.6, 127.1, 116.1, 79.1, 53.7, 48.6, 45.2, 43.2, 36.6, 22.4. XRPD (2θ):

main peaks at 14.7, 14.8, 17.7, 18.3, 18.7, 19.2, 19.8, 21.5, 24.4, 25.1, 25.9, 26.2, 27.3, 33.1±0.2.

Example 2

Preparation of (R)-zopiclone N-acetyl-D-aspartate 160 ml of a mixture of methanol/toluene at atmospheric pressure were distilled from the mother liquors of the preparation of the example 1. A light brown solid crystallized from the resulting mixture. The dispersion was cooled at room temperature. The solid was isolated by filtration and washed with 10 ml of methanol and 10 ml of toluene. The product was dried under vacuum to obtain 15.8 g of white solid (R)-zopiclone N-acetyl-D-aspartate (44%) as an off-white solid.

d.e.: 86.3% by chiral HPLC. Water content: 6.3% w/w. Melting point: 176-177° C. $[\alpha]_D^{20}$: −72.5° (c 1% w/w water). IR (KBr, cm$^{-1}$): 3433, 3068, 2860, 1741, 1732, 1720, 1675, 1577, 1461, 1373, 1255, 1144, 1052, 975. $^1$H-NMR (DMSO-d$_6$, 400 MHz) δ (ppm): 8.96 (1H, d, 2.8 Hz), 8.93 (1H, d, 2.8 Hz), 8.52 (1H, d, 2.8 Hz), 8.36 (1H, d, 9.2 Hz), 8.10 (1H, wide signal), 8.09 (1H, dd, 9.2 Hz, 2.8 Hz), 7.76 (1H, s), 4.46-4.41 (1H, m), 3.47 (1H, wide signal), 3.31 (1H, wide signal), 3.14 (2H, wide signal), 2.62 (1H, dd, 16.4 Hz, 6.0 Hz), 2.50 (1H, dd, 16.4 Hz, 6.4 Hz), 2.40 (1H, wide signal), 2.32 (1H, wide signal), 2.19 (1H, wide signal), 2.16 (3H, s), 1.88 (1H, wide signal), 1.81 (3H, s). $^{13}$C-NMR (DMSO-d$_6$, 100 MHz) δ (ppm): 172.7, 171.8, 169.0, 163.1, 155.4, 152.8, 148.6, 148.0, 147.8, 146.6, 143.4, 138.6, 127.1, 116.1, 79.1, 53.7, 48.6, 45.2, 43.3, 36.6, 22.4. XRPD (2θ): main peaks at 5.3, 8.0, 10.6, 12.7, 14.1, 15.8, 15.9, 17.1, 21.3, 24.2, 24.8, 25.5, 25.8±0.2.

Example 3

Preparation of (R)-zopiclone N-acetyl-L-aspartate

A three-neck 100 ml flask was charged with 2 g of (±)-zopiclone (1 eq) and 0.9 g of N-acetyl-L-aspartic acid (1 eq), and a mixture of 29 ml of methanol/xylene (1/1) were added. The reaction mixture was stirred for 10 minutes at room temperature, then heated and maintained for 30 minutes at reflux, and then was cooled and the dispersion was maintained for over 30 minutes at room temperature. The solid product was isolated by filtration and washed with 0.8 ml of methanol and 0.8 ml of xylene. The product was dried under vacuum to obtain 1.18 g of (R)-zopiclone N-acetyl-L-aspartate (41%) as a white solid.

d.e.: 91.8% by chiral HPLC. Water content: 0.6% w/w. Melting point: 184-186° C. $[\alpha]_D^{20}$: −57.5° (c 1% w/w water). IR (KBr, cm$^{-1}$): 3413, 3060, 2964, 1732, 1720, 1661, 1467, 1376, 1258, 1169, 1079. $^1$H-NMR (DMSO-d$_6$, 400 MHz) δ (ppm): 8.96 (1H, d, 2.4 Hz), 8.93 (1H, d, 2.4 Hz), 8.52 (1H, d, 2.4 Hz), 8.36 (1H, d, 9.2 Hz), 8.10 (1H, wide signal), 8.09 (1H, dd, 9.2 Hz, 2.4 Hz), 7.76 (1H, s), 4.46-4.40 (1H, m), 3.47 (1H, wide signal), 3.31 (1H, wide signal), 3.14 (2H, wide signal), 2.62 (1H, dd, 16.4 Hz, 6.4 Hz), 2.50 (1H, dd, 16.4 Hz, 6.4 Hz), 2.39 (1H, wide signal), 2.31 (1H, wide signal), 2.19 (1H, wide signal), 2.15 (3H, s), 1.85 (1H, wide signal), 1.81 (3H, s). $^{13}$C-NMR (DMSO-d$_6$, 100 MHz) δ (ppm): 172.7, 171.9, 169.0, 163.1, 155.4, 152.8, 148.6, 148.0, 147.8, 146.6, 143.4, 138.6, 127.1, 116.1, 79.1, 53.8, 48.6, 45.2, 43.3, 36.7, 22.4. XRPD (2θ): main peaks at 14.7, 14.8, 18.3, 18.7, 19.2, 19.8, 21.5, 21.5, 24.4, 25.1, 25.9, 26.2, 27.3±0.2.

Example 4

Preparation of (R)-zopiclone N-acetyl-L-aspartate

A three-neck 250 ml flask was charged with 10 g of (±)-zopiclone (1 eq) and 4.5 g of N-acetyl-L-aspartic acid (1 eq). 87 ml of a mixture of methanol/toluene (1/1) were added. The reaction mixture was stirred for 3 minutes at room temperature, then heated and maintained for 10 minutes at reflux temperature. The dispersion was slowly cooled and maintained for over 1 hour at room temperature. The solid product was isolated by filtration and washed with 10 ml of methanol and 10 ml of toluene. The product was dried under vacuum to obtain 6.7 g of (R)-zopiclone N-acetyl-L-aspartate (46%) as a white solid.

d.e.: 96.6% by chiral HPLC. Water content: 0.2% w/w. Melting point: 181-186° C. $[\alpha]_D^{20}$: −62.5°(c 1% w/w water). IR (KBr, cm$^{-1}$): 3433, 3067, 3006, 2860, 1740, 1731, 1720, 1675, 1576, 1460, 1373. $^1$H-NMR (DMSO-d$_6$, 400 MHz) δ (ppm): 8.98 (1H, d, 2.8 Hz), 8.95 (1H, d, 2.8 Hz), 8.54 (1H, d, 2.4 Hz), 8.38 (1H, d, 8.4 Hz), 8.14 (1H, wide signal), 8.11 (1H, dd, 8.4 Hz, 2.4 Hz), 7.79 (1H, s), 4.49-4.43 (1H, m), 3.48 (1H, wide signal), 3.32 (1H, wide signal), 3.10 (2H, wide signal), 2.63 (1H, dd, 16.4 Hz, 6.0 Hz), 2.52 (1H, dd, 16.4 Hz, 6.4 Hz), 2.42 (1H, wide signal), 2.33 (1H, wide signal), 2.195 (1H, wide signal), 2.18 (s, 3H), 1.91 (1H, wide signal), 1.83 (3H, s). $^{13}$C-NMR (DMSO-d$_6$, 100 MHz) δ (ppm): 172.7, 171.8, 169.0, 163.1, 155.4, 152.8, 148.6, 148.0, 147.8, 146.6, 143.4, 138.6, 127.0, 116.1, 79.1, 53.7, 48.6, 45.2, 43.2, 36.6, 22.4. XRPD (2θ): main peaks at 14.7, 18.3, 18.7, 19.2, 19.8, 21.4, 21.5, 25.1, 25.9, 26.2, 27.3±0.2.

Example 5

Preparation of (S)-zopiclone N-acetyl-L-aspartate 80 ml of methanol/toluene of mother liquors of the preparation of (R)-zopiclone N-acetyl-L-aspartate of the example 4 were distilled at atmospheric pressure and white solid crystallized from the resulting mixture. 20 ml of fresh toluene were added. The mixture was cooled to room temperature and maintained for over 30 minutes at this temperature. The product was isolated by filtration, washed twice with 10 ml of toluene and dried under vacuum to obtain 6.2 g of (S)-zopiclone N-acetyl-L-aspartate (43%) as a white solid.

d.e.: 92.3% by chiral HPLC. Water content: 4.3% w/w. Melting point: 173-179° C. $[\alpha]_D^{20}$: +93° (c 0.4% w/w acetone). IR (KBr, cm$^{-1}$): 3436, 3059, 3025, 2968, 1743, 1732, 1724, 1660, 1470, 1377, 1079. $^1$H-NMR (DMSO-d$_6$, 400 MHz), δ (ppm): 8.98 (1H, d, 2.8 Hz), 8.95 (1H, d, 2.8 Hz), 8.54 (1H, d, 2.8 Hz), 8.38 (1H, d, 9.2 Hz), 8.14 (1H, wide signal), 8.11 (1H, dd, 9.2 Hz, 2.8 Hz), 7.84 (1H, s), 4.48-4.43 (1H, m), 3.48 (1H, wide signal), 3.33 (1H, wide signal) 3.16 (2H, wide signal), 2.63 (1H, dd, 16.4 Hz, 6.4 Hz), 2.52 (1H, dd, 16.4 Hz, 6.8 Hz), 2.41 (1H, wide signal), 2.333 (1H, wide signal), 2.18 (s, 3H), 2.17 (1H, wide signal), 1.91 (1H, wide signal), 1.83 (3H, s). $^{13}$C-NMR (DMSO-d$_6$, 100 MHz), δ (ppm): 172.7, 171.8, 169.0, 163.1, 155.4, 152.8, 148.6, 148.0, 147.8, 146.6, 143.4, 138.6, 127.0, 116.1, 79.1, 53.7, 48.6, 45.2, 43.3, 36.6, 22.4. XRPD (2θ): main peaks at 5.3, 7.9, 10.6, 12.7, 15.7, 17.0, 17.1, 17.3, 18.8, 21.3, 24.3, 24.8, 25.6, 26.4, 29.1±0.2.

Example 6

Preparation of (S)-zopiclone N-acetyl-D-glutamate

A reaction flask was charged with 11.2 g of (±)-zopiclone (1 eq), 4.9 g of N-acetyl-D-glutamic acid (0.9 eq) and 830 ml of acetone. The mixture was heated to reflux and the dispersion was maintained for 1 hour at this temperature. The warm solution was filtered to obtain a clear solution. The solution was concentrated to one half at atmospheric pressure. The solution was cooled and at about 46° C. white solid crystallizes. The slurry was cooled at room temperature and maintained for 30 minutes. The solid product was isolated by filtration and washed with 2 ml of acetone. The product was dried under vacuum to obtain 5.9 g of (S)-zopiclone N-acetyl-D-glutamate (40%) as a white solid.

d.e.: 89.7% by chiral HPLC. Water content: 0.75% w/w. Melting point: 169-171° C. $[\alpha]_D^{20}$: +60° (c 1% w/w water). IR (KBr, cm$^{-1}$): 3422, 3334, 3003, 2941, 2875, 1758, 1724, 1670, 1578, 14601, 1374, 1086. $^1$H-NMR (DMSO-d$_6$, 400 MHz) δ (ppm): 8.98 (1H, d, 2.4 Hz), 8.95 (1H, d, 2.4 Hz), 8.54 (1Hd, 2.8 Hz), 8.38 (1H, d, 9.2 Hz), 8.11 (1H, dd, 9.2 Hz, 2.8 Hz), 8.10 (1H, wide signal) 7.79 (1H, s), 4.20-4.15 (1H, m), 3.48 (1H, wide signal), 3.29 (1H, wide signal), 3.13 (2H, wide signal), 2.40-2.20 (4H, m), 2.11 (3H, s), 2.08 (1H, wide signal), 1.94 (1H, m), 1.84 (3H, s), 1.81-1.71 (2H, m). $^{13}$C-NMR (DMSO-d$_6$, 100 MHz), δ (ppm): 173.7, 173.5, 169.3, 163.1, 155.4, 152.8, 148.6, 148.0, 147.7, 146.6, 143.4, 138.6, 127.0, 116.1, 79.1, 53.9, 51.2, 45.5, 43.5, 30.2, 26.4, 22.3. XRPD (2θ): main peaks at 3.4, 12.1, 13.6, 17.0, 18.4, 18.9, 19.1, 19.2, 19.8, 20.08, 20.4, 22.0, 22.9, 24.1, 24.5, 25.4, 26.5, 27.3±0.2.

Example 7

Preparation of (R)-zopiclone N-acetyl-L-glutamate

A reaction flask was charged with 5 g of (±)-zopiclone (1 eq), 2.4 g of N-acetyl-L-glutamic acid (1 eq) and 186 ml of acetone. The mixture was heated to reflux and the dispersion was maintained for 30 min. at this temperature. The solution was cooled at 35-37° C. and maintained 30 min. The suspension was cooled at room temperature. The product was isolated by filtration and washed twice with 5 ml of acetone. The product was dried under vacuum to obtain 3.6 g of (R)-zopiclone N-acetyl-L-glutamate (48%) as a white solid.

d.e.: 89.2% by chiral HPLC. $^1$H-NMR (DMSO-d$_6$, 400 MHz) δ (ppm): 8.96 (1H, d, 2.4 Hz), 8.93 (1H, d, 2.4 Hz), 8.52 (1H, d, 2.8 Hz), 8.36 (1H, d, 8.8 Hz), 8.10 (1H, dd, 8.8 Hz, 2.8 Hz), 8.08 (1H, wide signal) 7.76 (1H, s), 4.18-4.13 (1H, m), 3.46 (1H, wide signal), 3.28 (1H, wide signal), 3.11 (2H, wide signal), 2.31-2.20 (4H, m), 2.10 (3H, s), 2.07 (1H, wide signal), 1.96-1.89 (1H, m), 1.82 (3H, s), 1.80-1.70 (2H, m).

Example 8

Preparation of (S)-zopiclone N-acetyl-D-methionate

A reaction flask was charged with 10.2 g of (±)-zopiclone (1 eq), 5 g of N-acetyl-D-methionine (1 eq) and 300 ml of ethyl acetate. The mixture was heated to reflux and the solution was maintained for 30 min. at this temperature. The solution was cooled and at about 66° C. solid crystallized. The suspension was cooled and maintained for 1 hour at room temperature. The product was isolated by filtration and washed twice with 3 ml of ethyl acetate. The product was dried under vacuum to obtain 6.9 g of (S)-zopiclone N-acetyl-D-methionate (46%) as a white solid.

d.e.: 98.4% by chiral HPLC. Water content: 0.09% w/w. Melting point: 171-172° C. $[\alpha]_D^{20}$: +77.5° (c 1% w/w acetone). IR (KBr, cm$^{-1}$): 3292, 3064, 2915, 1740, 1731, 1720, 1668, 1461, 1373, 1090. $^1$H-NMR (DMSO-d$_6$, 400 MHz) δ (ppm): 8.98 (1H, d, 2.8 Hz), 8.95 (1H,d, 2.8 Hz), 8.54 (1H, d, 2.8 Hz), 8.37 (1H, d, 9.2 Hz), 8.13 (1H, wide signal), 8.11 (1H, dd, 9.2 Hz, 2.8 Hz), 7.79 (1H, s), 4.30-4.24 (1H, m), 3.47 (1H, wide signal), 3.28 (1H, wide signal), 3.13 (2H, wide signal), 2.51-2.43 (2H, m), 2.31 (1H, wide signal), 2.22 (1H, wide signal), 2.11 (3H, s), 2.06 (1H, wide signal), 2.03 (3H, s), 1.95-1.93 (1H, m), 1.84 (3H, s), 1.81-1.71 (2H, m). $^{13}$C-NMR (DMSO-d$_6$, 100 MHz), δ (ppm): 173.5, 169.4, 163.1, 155.4, 152.8, 148.6, 148.0, 147.7, 146.6, 143.4, 138.6, 127.0, 116.1, 79.1, 54.0, 51.0, 45.6, 43.6, 30.7, 29.7, 22.4, 14.5. XRPD (2θ): main peaks at 3.3, 6.5, 11.8, 13.0, 13.9, 18.5, 18.7, 19.0, 19.1, 19.3, 19.8, 20.0, 22.0, 22.2, 26.4, 27.1±0.2.

Example 9

Preparation of (R)-zopiclone N-acetyl-D-methionate 290 ml of ethyl acetate at atmospheric pressure were distilled from the mother liquors of the preparation of (S)-zopiclone N-acetyl-D-methionate of the example 8. The product crystallized from the concentrate solution at about 32° C. The mixture was cooled to room temperature and maintained for over 30 minutes. The product was isolated by filtration and washed twice with 3 ml of ethyl acetate. The product was dried under vacuum obtaining 4.2 g of (R)-zopiclone N-acetyl-D-methionate (28%) as an off-white solid.

d.e.: 82.6% by chiral HPLC. Water content: 1.7% w/w. Melting point: 162-164° C. $[\alpha]_D^{20}$: −95° (c 1% w/w water). IR (KBr, cm$^{-1}$): 3447, 3305, 2942, 2790, 1740, 1730, 1716, 1668, 1659, 1655, 1462, 1372, 1143, 1046. $^1$H-NMR (DMSO-d$_6$, 400 MHz) δ (ppm): 8.96 (1H, d, 2.8 Hz), 8.93 (1H,d, 2.8 Hz), 8.5 (1H, d, 2.8 Hz), 8.36 (1H, d, 9.2 Hz), 8.11 (1H, wide signal), 8.09 (1H, dd, 9.2 Hz, 2.8 Hz), 7.77 (1H, s), 4.27-44.22 (1H, m), 3.45 (1H, wide signal), 3.26 (1H, wide signal), 3.11 (2H, wide signal), 2.49-2.30 (2H, m), 2.30 (1H, wide signal), 2.19 (1H, wide signal), 2.08 (3H, s), 2.04 (1H, wide signal), 2.01 (3H, s), 1.92-1.89 (1H, m), 1.82 (3H, s), 1.79-1.69 (2H, m). $^{13}$C-NMR (DMSO-d$_6$, 100 MHz), δ (ppm): 173.5, 169.4, 163.1, 155.4, 152.8, 148.6, 148.0, 147.7, 146.6, 143.4, 138.6, 127.0, 116.1, 79.1, 54.0, 51.0, 45.6, 43.6, 30.7, 29.7, 22.4, 14.5. XRPD (2θ): main peaks at 3.3, 3.4, 11.9, 16.0, 16.7, 18.2, 18.8, 18.9, 20.0, 20.7, 21.3, 21.6, 25.3, 25.6, 25.8, 26.1, 26.9, 27.6±0.2.

Example 10

Preparation of Eszopiclone from (S)-zopiclone N-acetyl-L-aspartate 45 ml of dichloromethane were added to a solution of 3 g of (S)-zopiclone N-acetyl-L-aspartate in 6 ml of water at room temperature. The mixture is basified to pH 10 with a solution of 40% aqueous potassium carbonate. The aqueous layer is decanted and extracted with 45 ml of dichloromethane. Organic layers were joined together and concentrated under vacuum until dryness obtaining 2.04 g of eszopiclone (100%) as a white solid.

Enantiomeric excess (e.e.): 99.3% by chiral HPLC. Water content: 0.02% w/w. Melting point: 190-192° C. $[\alpha]_D^{20}$: +115° (c 1% w/w acetone). IR (KBr, cm$^{-1}$): 2942, 2790, 1730, 1715, 1470, 1463, 1372, 1086. $^1$H-NMR (DMSO-d$_6$, 400 MHz) δ (ppm): 8.98 (1H, d, 2.8 Hz), 8.95 (1H, d, 2.8 Hz), 8.53 (1H, d, 2.8 Hz), 8.37 (1H, d, 9.2 Hz), 8.10 (1H, dd, 9.2

Hz, 2.8 Hz), 7.79 (1H, s), 3.47 (1H, wide signal), 3.26 (1H, wide signal), 3.12 (2H, wide signal), 2.30 (1H, wide signal), 2.20 (1H, wide signal), 2.09 (3H, s), 2.04 (1H, wide signal), 1.76 (1H, wide signal). $^{13}$C-NMR (DMSO-$d_6$, 100 MHz), δ (ppm): 163.1, 155.4, 152.8, 148.6, 148.0, 147.8, 146.6, 143.4, 138.6, 127.0, 116.1, 79.1, 54.0, 45.7, 43.6. XRPD (2θ): main peaks at 9.9, 12.5, 16.0, 16.1, 18.0, 19.0, 20.1, 21.3, 25.6, 25.8, 27.6, 29.8±0.2.

Example 11

Preparation of (R)-zopiclone from (R)-zopiclone N-acetyl-L-aspartate 6 ml of water and 45 ml of dichloromethane were added to 3 g of (R)-zopiclone N-acetyl-L-aspartate at room temperature. The mixture is basified to pH 10 with a solution of 40% aqueous potassium carbonate. The aqueous layer is decanted and extracted with 45 ml of dichloromethane. The combined organic layers were concentrated under vacuum until dryness obtaining 2.15 g of (R)-zopiclone (100%) as a white solid.

e.e.: 100% by chiral HPLC. $[α]_D^{20}$: −125° (c 1% w/w acetone). IR (KBr, cm$^{-1}$): 2942, 2790, 1730, 1715, 1462, 1371, 1086. $^1$H-NMR (DMSO-$d_6$, 400 MHz) δ (ppm): 8.98 (1H, d, 2.4 Hz), 8.95 (1H, d, 2.4 Hz), 8.53 (1H, d, 2.8 Hz), 8.37 (1H, d, 9.2 Hz), 8.11 (1H, dd, 9.2 Hz, 2.8 Hz), 7.79 (1H, s), 3.50 (1H, wide signal), 3.26 (1H, wide signal), 3.12 (2H, wide signal), 2.30 (1H, wide signal), 2.20 (1H, wide signal), 2.09 (3H, s), 2.04 (1H, wide signal), 1.76 (1H, wide signal). $^{13}$C-NMR (DMSO-$d_6$, 100 MHz), δ (ppm): 163.0, 155.4, 152.8, 148.6, 148.0, 147.7, 146.6, 143.4, 138.6, 127.0, 116.1, 79.1, 54.0, 45.7, 43.6. XRPD (2θ): main peaks at 5.0, 9.9, 12.5, 16.0, 16.1, 18.0, 19.0, 20.0, 21.3, 25.6, 27.6, 29.7±0.2.

Example 12

Preparation of Eszopiclone from (S)-zopiclone N-acetyl-D-aspartate 2.7 ml of a 40% aqueous solution of potassium carbonate were added to a solution of 2 g of (S)-zopiclone N-acetyl-D-aspartate in 18 ml of water in about 30 minutes at room temperature. The slurry was maintained for 1.5 hours at this temperature. The product was isolated by filtration and washed twice with 1.4 ml of water. The product was dried under vacuum at room temperature obtaining 1.29 g of eszopiclone (94%) as a white solid.

e.e.: 99.8% by chiral HPLC. Water content: 0.9% w/w. Melting point: 198-201° C. $[α]_D^{20}$: +145° (c 1% w/w acetone).

Example 13

Crystallization of Eszopiclone 1 g of crude eszopiclone was dissolved in 15 ml of methyl isobutyl ketone (MIBK) at about 114° C. The solution was cooled and seeded. The solid crystallized at about 98-100° C., the slurry was maintained for 30 minutes at this temperature. Then it was cooled at room temperature. The product was isolated by filtration and washed twice with 0.4 ml MIBK. The product was dried under vacuum obtaining 0.85 g of eszopiclone (85%).

e.e.: 100% by chiral HPLC. Melting point: 195-198° C. $[α]_D^{20}$: +140° (c 1% w/w acetone).

Example 14

Crystallization of Eszopiclone 2.2 g of crude eszopiclone were dissolved in 44 ml of methyl ethyl ketone (MEK) at about 76° C. The warm solution was filtered and 23 ml of MEK were distilled. The solution was cooled at −5° C. and maintained for 30 minutes at this temperature. The product was isolated by filtration and washed twice with 0.4 ml MEK. The product was dried under vacuum obtaining 2.0 g of eszopiclone (91%).

e.e.: 100% by chiral HPLC. Melting point: 202-204° C. $[α]_D^{20}$: +135° (c 1% w/w acetone).

The invention claimed is:

1. An optically pure diastereoisomeric salt of formula (II):

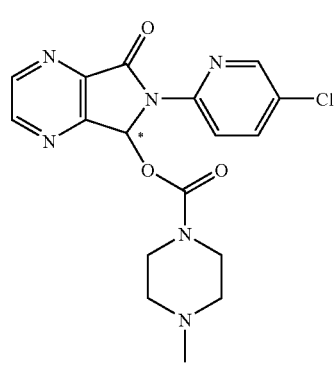

(I)

wherein HX is an optically active acetylated amino acid of formula (III):

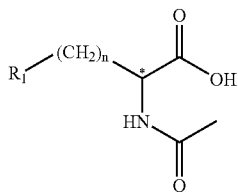

(III)

wherein:
 n is 0, 1, 2 or 3,
 $R^1$ is H, an alkyl group, an aryl group, a heteroaryl group, $CONH_2$, COOH, $SR^2$ or $OR^2$,
 wherein $R^2$ is a $C_1$-$C_6$ alkyl.

2. A salt according to claim 1 which is one of (S)-zopiclone N-acetyl-D-glutamate, (S)-zopiclone N-acetyl-D-aspartate, or (S)-zopiclone N-acetyl-D-methionate.

3. A salt according to claim 1 which is one of (S)-zopiclone N-acetyl-L-glutamate, (S)-zopiclone N-acetyl-L-aspartate, or (S)-zopiclone N-acetyl-L-methionate.

4. A salt according to claim 1 which is one of (R)-zopiclone N-acetyl-D-glutamate, (R)-zopiclone N-acetyl-D-aspartate, or (R)-zopiclone N-acetyl-D-methionate.

5. A salt according to claim 1 which is one of (R)-zopiclone N-acetyl-L-glutamate, (R)-zopiclone N-acetyl-L-aspartate, or (R)-zopiclone N-acetyl-L-methionate.

* * * * *

UNITED STATES PATENT AND TRADEMARK OFFICE
CERTIFICATE OF CORRECTION

PATENT NO.        : 7,772,396 B2
APPLICATION NO.   : 11/866584
DATED             : August 10, 2010
INVENTOR(S)       : David Fernández Bleda and Jordi Lluis Tous Page 1 of 1

It is certified that error appears in the above-identified patent and that said Letters Patent is hereby corrected as shown below:

<u>Column 14,</u>

Line 15, change "(I)" to -- (II) --.

Line 20, change " 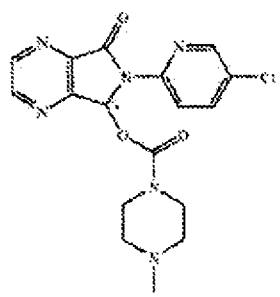 " to -- 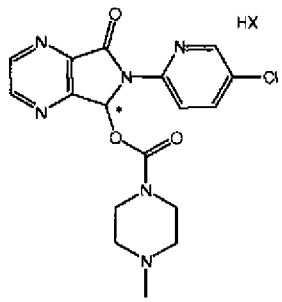 --.

Signed and Sealed this
Twenty-ninth Day of May, 2012

David J. Kappos
*Director of the United States Patent and Trademark Office*